United States Patent
Smutney et al.

(10) Patent No.: US 6,837,878 B2
(45) Date of Patent: Jan. 4, 2005

(54) BLUNTABLE NEEDLE ASSEMBLY WITH OPEN-ENDED BLUNTING PROBE

(75) Inventors: Chad C. Smutney, Stafford Springs, CT (US); John M. Polidoro, Coventry, CT (US)

(73) Assignee: ICU Medical, Inc., San Clemente, CA (US)

( * ) Notice: Subject to any disclaimer, the term of this patent is extended or adjusted under 35 U.S.C. 154(b) by 16 days.

(21) Appl. No.: 09/757,138

(22) Filed: Jan. 9, 2001

(65) Prior Publication Data

US 2002/0095123 A1 Jul. 18, 2002

(51) Int. Cl.$^7$ .......................... A61M 5/32; A61M 5/178
(52) U.S. Cl. ............ 604/272; 604/164.01; 604/164.02; 604/164.06; 604/198; 604/158
(58) Field of Search .................................. 604/192, 158, 604/198, 160–171, 264–274, 110, 506, 187

(56) References Cited

U.S. PATENT DOCUMENTS

| | | | |
|---|---|---|---|
| 4,627,841 A | 12/1986 | Dorr | 604/158 |
| 4,828,547 A * | 5/1989 | Sahi et al. | 604/110 |
| 5,009,642 A | 4/1991 | Sahi | 604/158 |
| 5,092,851 A | 3/1992 | Ragner | 604/192 |
| 5,312,345 A | 5/1994 | Cole | 604/110 |
| 5,480,389 A * | 1/1996 | McWha et al. | 604/158 |
| 5,697,914 A | 12/1997 | Brimhall | 604/177 |
| 5,743,882 A | 4/1998 | Luther | 604/168 |
| 5,817,060 A | 10/1998 | Overton et al. | 604/164 |
| 5,951,520 A | 9/1999 | Burzynski et al. | 604/170 |
| 6,056,726 A * | 5/2000 | Isaacson | 604/164.01 |
| 6,106,499 A | 8/2000 | Overton et al. | 604/170.01 |
| 6,254,574 B1 * | 7/2001 | Burzynski et al. | 604/170.01 |
| 6,391,007 B2 * | 5/2002 | Chang et al. | 604/164.01 |
| 6,544,239 B2 * | 4/2003 | Kinsey et al. | 604/272 |
| 6,623,456 B1 | 9/2003 | Holdaway et al. | 604/164.08 |

* cited by examiner

*Primary Examiner*—Brian L. Casler
*Assistant Examiner*—Roz Maiorino
(74) *Attorney, Agent, or Firm*—Knobbe Martens Olson & Bear LLP (57) ABSTRACT

A needle assembly includes a needle component (10) and a blunting component (26), the needle component (10) containing a needle cannula (12) mounted in a housing (16) which defines a fluid chamber such as a fluid chamber (20). The blunting component (26) contains a non-perforated, open-ended blunting probe (28) mounted in a shuttle (30). The needle cannula (12) and the blunting probe (28) are disposed telescopically one within the other without obstructing flow through the needle passageway, and are movable between a sharpened configuration and a blunted configuration. The blunting member (26) is configured to permit the open end of the blunting probe (28) to provide flow access to the fluid chamber (20) in the housing (16).

10 Claims, 7 Drawing Sheets

BLUNTABLE NEEDLE ASSEMBLY WITH OPEN-ENDED BLUNTING PROBE

BACKGROUND OF THE INVENTION

1. Field of the Invention

The present invention pertains to self-blunting medical needles and, in particular, to needle assemblies in which an internal blunting component provides a flow path to the surrounding needle housing.

2. Related Art

Many accidental needle-stick wounds are sustained by healthcare workers each day. The problem is aggravated by the trend of moving treatment out of hospitals and into doctors' offices and neighborhood clinics as part of programs to reduce healthcare costs. This trend increases the number and dispersion of healthcare workers who administer injections and draw blood samples, while reducing the frequency of such injections per individual healthcare worker. As a consequence, a larger number of less experienced people are administering injections and/or taking blood samples. Although in the past an occasional serious illness such as that caused by the hepatitis B virus was sustained as a result of an accidental needle-stick wound, the problem was not considered to be a serious one until the advent of human immunodeficiency virus (HIV) and the knowledge that this virus is transmissible to healthcare workers through needle-stick wounds from a contaminated needle. HIV causes acquired immune deficiency syndrome (AIDS) which has already killed millions and infected millions more. HIV is often referred to simply as "the AIDS virus" and the Surgeon General of the United States of America noted in a published (September, 1987) interview that there is no better way to become infected with the AIDS virus than to take blood from an AIDS patient and accidentally inflict a needle-stick wound with the contaminated needle. This situation, and the rising incidence of hepatitis C, another blood-transmissible disease, has stimulated activity to develop devices which reduce or eliminate the possibility of accidental needle-stick wounds without excessively increasing the unit cost of needles.

In some prior art bluntable needle assemblies, the blunting member is open to fluid flow into a fluid chamber (e.g., a flash chamber) of the needle component by virtue of perforations in the blunting member, while the end of the blunting member is sealed off within a shuttle structure which is accessible externally of the needle component. For example, U.S. Pat. No. 5,817,060 to Overton et al, issued Oct. 6, 1998 and entitled "Unidirectional Blunting Apparatus For Hypodermic Needles", discloses a blunting apparatus for hypodermic needles. As seen in FIG. 5, the needle cannula 26 is mounted in a hub 32 which defines a fluid chamber (bore 34). The blunting member 40 extends into the cannula from a shuttle (positioning member 44). The shuttle is disposed partially within the fluid chamber but it also protrudes outwards to provide a surface 50 by which the blunting member can be moved from outside the chamber. The end of the blunting member is not open for fluid flow to the chamber, so the blunting member is perforated for this purpose (apertures 48). A similar arrangement is seen in U.S. Pat. No. 5,743,882 to Luther, issued Apr. 28, 1998 and entitled "Needle Blunting Assembly For Use With Intravascular Introducers" (see FIGS. 4 and 5) and in U.S. Pat. No. 5,697,914 to Brimhall, issued Dec. 16, 1997 and entitled "Control Forward/Flashback Forward One Hand Introducer Needle and Catheter Assembly", although in the Brimhall Patent the relative positions of the catheter (which is analogous to a blunting member) and the needle cannula are reversed (see FIG. 2).

In other prior art assemblies, the end of the blunting member is open to fluid flow into the needle component chamber, but the shuttle is wholly enclosed within the needle component. For example, the Bio-Plexus, Inc. Patent to Burzynski et al, U.S. Pat. No. 5,951,520, issued Sep. 14, 1999 and entitled "Self-Blunting Needle Medical Devices And Methods Of Manufacture Thereof", discloses a self-blunting needle assembly in which the needle component defines a fluid chamber (within syringe body 102) and the end of the blunting component is open to fluid flow to the chamber. However, the blunting component shuttle (hub 16) does not extend outside the fluid chamber for access from outside the chamber.

In still other prior art devices, the end of the blunting member is open and fluid can flow therethrough but there is no fluid flow communication from the blunting member to a fluid chamber on the needle holder or the blunting member shuttle. This configuration is illustrated in U.S. Pat. No. 4,627,841 to Dorr, issued Dec. 9, 1986 and entitled "Infusion Needle", where it is seen that the blunting component or "catheter" 17 is mounted in a bore in hub 12 which perforates, i.e., extends through, the hub and therefore has two open ends. Catheter 17 is disposed concentrically within needle cannula 14 and the rearward end 19 open for fluid flow. However, the needle holder (hub 11, FIG. 4) and hub 12 do not define a flash chamber and the open end of the blunting component.

SUMMARY OF THE INVENTION

The present invention pertains to a bluntable needle assembly comprising a needle component comprising a housing and a needle cannula mounted on the housing, the housing defining a fluid chamber and an access port for fluid flow therethrough. There is a blunting component comprising a shuttle member and a blunting probe mounted on the shuttle member, the blunting probe having a blunt tip and a rearward open end. The blunting probe is disposed within the needle cannula and the needle component and the blunting component are configured with the blunting probe within the needle cannula for movement from a sharpened configuration to locking engagement in a blunted configuration, and the shuttle member is configured to extend outside the fluid chamber and to permit fluid flow from the open end of the blunting probe into the fluid chamber.

According to one aspect of the invention, the blunting probe may be tubular and non-perforated.

According to another aspect of this invention, the needle assembly may comprise a component and a stay, the detent being movable between (i) a locking position in which it may bear against the stay and prevent the needle assembly from moving to the sharpened configuration and (ii) an unlocked position which permits the needle assembly to move to the sharpened configuration. Optionally, the shuttle may comprise the movable detent. Another optional feature of the invention is that the detent further comprises a coupling site for engagement by an accessory.

The housing may define a port into which a piston portion of the shuttle extends from outside the fluid chamber.

In one embodiment, the shuttle member may define a non-perforating cavity within which the blunting probe is mounted. In another embodiment, the shuttle member may be perforated to permit fluid flow from the open end of the blunting probe therein to the fluid chamber. In yet another embodiment, the shuttle member may comprise an extension connected to the blunting probe in a manner which permits fluid flow from the end of the blunting probe to the fluid chamber.

According to yet another aspect of this invention, a bluntable needle assembly may comprise a needle component comprising a housing and a needle cannula having a sharp tip mounted thereon, and a blunting component comprising a shuttle member with a blunting probe thereon. The shuttle member may define a fluid chamber and an access port for fluid flow therethrough. The blunting probe may have a blunt tip and a rearward end open to the fluid chamber. As with other embodiments described herein, the blunting probe is disposed within the needle cannula and the needle component and blunting component are configured for movement between a blunted configuration and a sharpened configuration.

DETAILED DESCRIPTION OF THE INVENTION AND PREFERRED EMBODIMENT THEREOF

The present invention pertains to the configuration of a hollow, open-ended blunting probe mounted on a shuttle structure in a needle assembly such that the end of the blunting probe is open for fluid flow. According to one embodiment of the invention, the end of the blunting probe is secured in a non-perforating cavity (e.g., a slot, well, etc.) formed in the shuttle structure. According to another embodiment, the blunting probe may simply be attached to the shuttle structure in a manner which leaves the end of the blunting probe open. According to still another embodiment, the blunting probe may be mounted in a bore which perforates the shuttle member to provide a flow path through the shuttle member. In each of these embodiments, the needle assembly comprises a fluid chamber into which fluid may flow from the open end of the blunting probe. The fluid chamber may be formed in the housing on which the needle is mounted or on the shuttle structure. The needle component and the blunting component of the needle assembly are preferably configured so that the blunting probe can be received telescopically within the needle cannula and can be moved from a blunting position in which the blunt end of the blunting probe protrudes forward beyond the insertion tip of the needle, to blunt the assembly, and a retracted position (the "sharpened configuration") in which the blunt tip of the blunting probe is withdrawn rearward into the needle, leaving the sharp needle tip exposed.

Since the open end of the blunting probe is open even though it is joined to the shuttle structure, the present invention can optionally be practiced with a non-perforated blunting probe (i.e., the blunting probe may consist of a hollow tube open only at the ends) and will still provide fluid flow from the blunting probe to the fluid chamber. This is advantageous because the step of perforating a blunting probe to permit such flow through the probe wall is an expensive processing step which may be omitted by the practice of the invention.

Figure 1A:
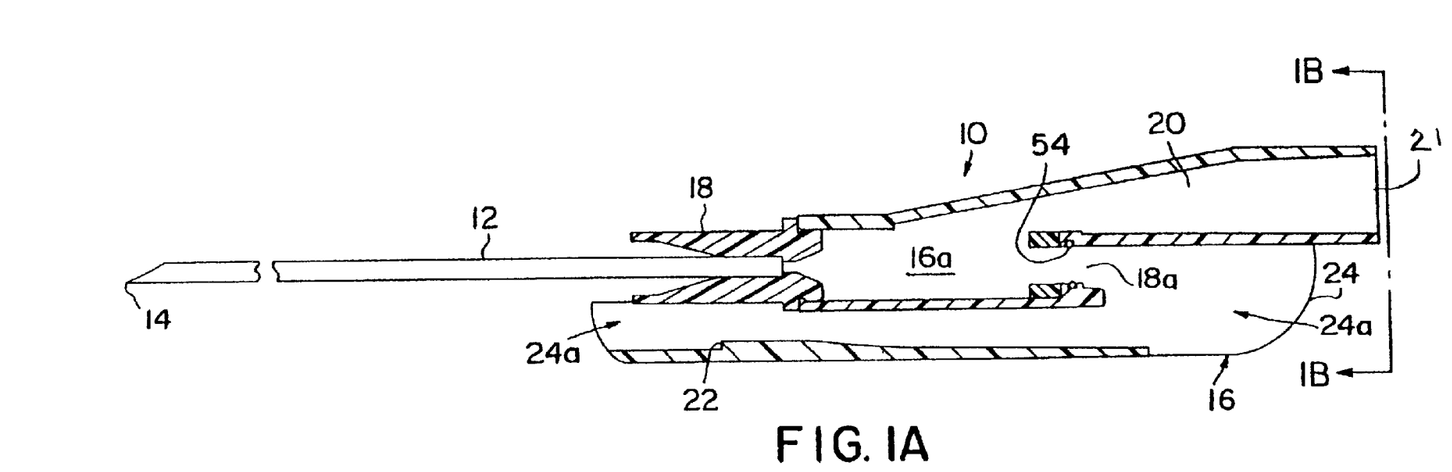
FIG. 1A is a schematic, partially cross-sectional view of a needle component configured for use in a particular embodiment of the present invention.
Figure 1B:
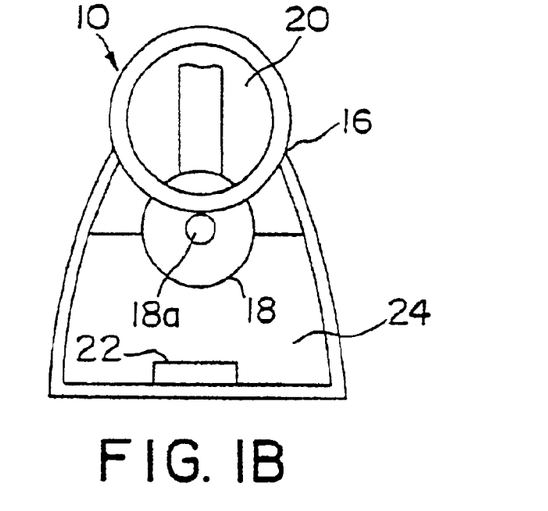
FIG. 1B is a schematic elevational view of the needle component of FIG. 1A, taken along line 1B—1B.

This invention can be embodied in various needle devices, including introducer needles for peripherally inserted central catheters. One embodiment of a needle component for a device in accordance with the present invention is shown in FIGS. 1A and 1B. Needle component 10 comprises a needle cannula 12 mounted in a housing 16. Needle cannula 12 has a sharp puncture tip 14 for penetrating a patient's skin and other tissues and a passageway (unnumbered) that extends through the cannula and which opens into a chamber 16a in housing 16. Needle component 10 is preferably dimensioned and configured to facilitate the handling of needle cannula 12 for convenient connection to other devices and may include structural features intended for specific environments of use. For example, when the device is intended for use in introducing a venal or arterial catheter, housing 16 may comprise a fluid chamber 20 into which blood can flow from needle cannula 12. Preferably, at least a portion of housing 16 is translucent or transparent so that the user can see blood flow into chamber 20 as a signal that needle cannula 12 is properly positioned, i.e., housing 16 may comprise a flash chamber for blood flash visualization. Optionally, chamber 20 may have an access port 21 for fluid flow therethrough. Port 21 is preferably configured to receive other devices such as a dosage syringe or fluid delivery tube or for luer access. Housing 16 also defines a port 18a for receiving the blunting component 26 (FIG. 2A) as described further below.

Needle component 10 (FIGS. 1A, 1B) may optionally be configured for a locking engagement with a blunting component. In the illustrated embodiment, needle component 10 comprises a stay 22 that will engage a blunting component as described below. Stay 22 may be positioned at any convenient point on needle component 10 but, in the illustrated embodiment, stay 22 is formed as the shoulder at the end of a sloped incline in a U-shaped guide 24 that is on housing 16 but outside of the chamber 16a.

Needle component 10 defines a port 18a which is preferably fitted with a bushing 54, for receiving the blunting component and through which a blunting probe may be inserted into needle cannula 12 via chamber 16a, as described below. Bushing 54 is an O-ring providing both a sealing function and a guiding function.

Figure 2A:
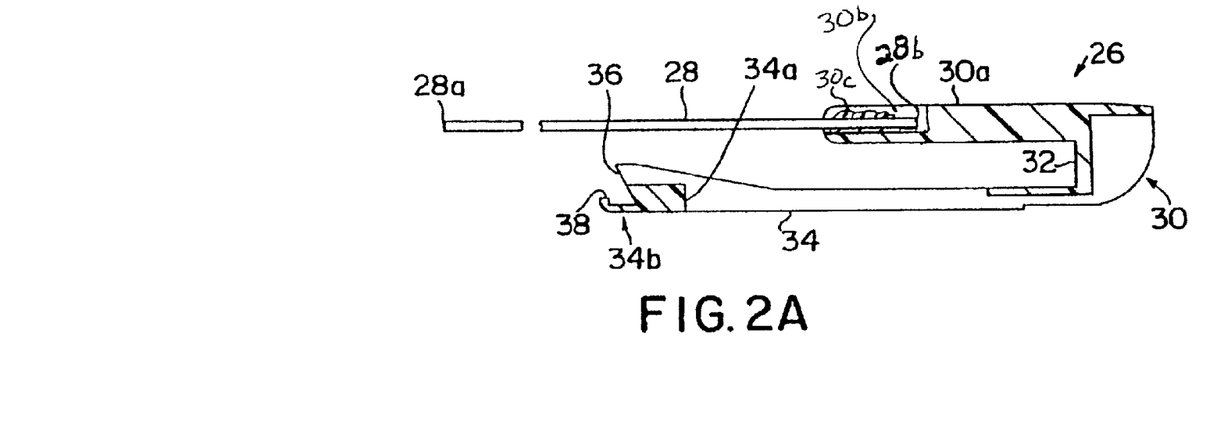
FIG. 2A is a schematic cross-sectional view of a particular embodiment of a blunting component for use with the needle component of FIG. 1A.
Figure 2B:
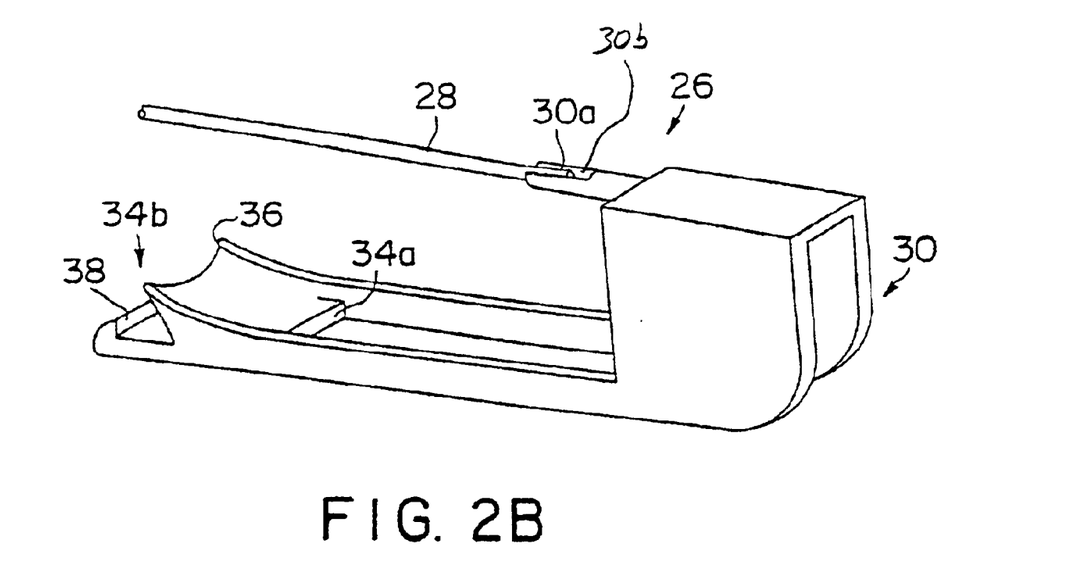
FIG. 2B is a perspective view of a blunting component intended for use with the needle component of FIG. 1A.

A blunting component in accordance with one embodiment of the present invention suitable for use with needle component 10 is shown in FIGS. 2A and 2B. Blunting component 26 comprises a hollow, unperforated blunting probe 28 that has a distal, open blunt tip 28a and an opposite open end 28b. Blunting probe 28 is carried on a shuttle 30. Shuttle 30 comprises a piston portion 30a and a base portion 32 which comprises a resilient, spring-like detent 34. Shuttle 30 has, in piston portion 30a, a non-perforating cavity for receiving the blunting probe 28. The non-perforating cavity comprises a slot 30b sized to receive blunting probe 28 therein. A bead of adhesive may be applied to blunting probe 28, near the open end and blunting probe 28 may then be positioned in slot 30b. The type and amount of adhesive 30c and the size of slot 30b and of blunting probe 28 which permit blunting probe 28 to be mounted in slot 30b without causing the adhesive to occlude the open end of blunting probe 28 can be readily determined by one of ordinary skill in the art without undue experimentation. Blunting probe 28 is disposed in slot 30b with its end open for fluid flow through slot 30b and the adhesive is then cured. A UV-curable adhesive has been found to work well in this approach, but any other type of suitable adhesive may be used. Thus, open end 28b is open to fluid flow into the slot and, from the slot, into a surrounding region in the needle member, as will be described further below.

Figure 3:
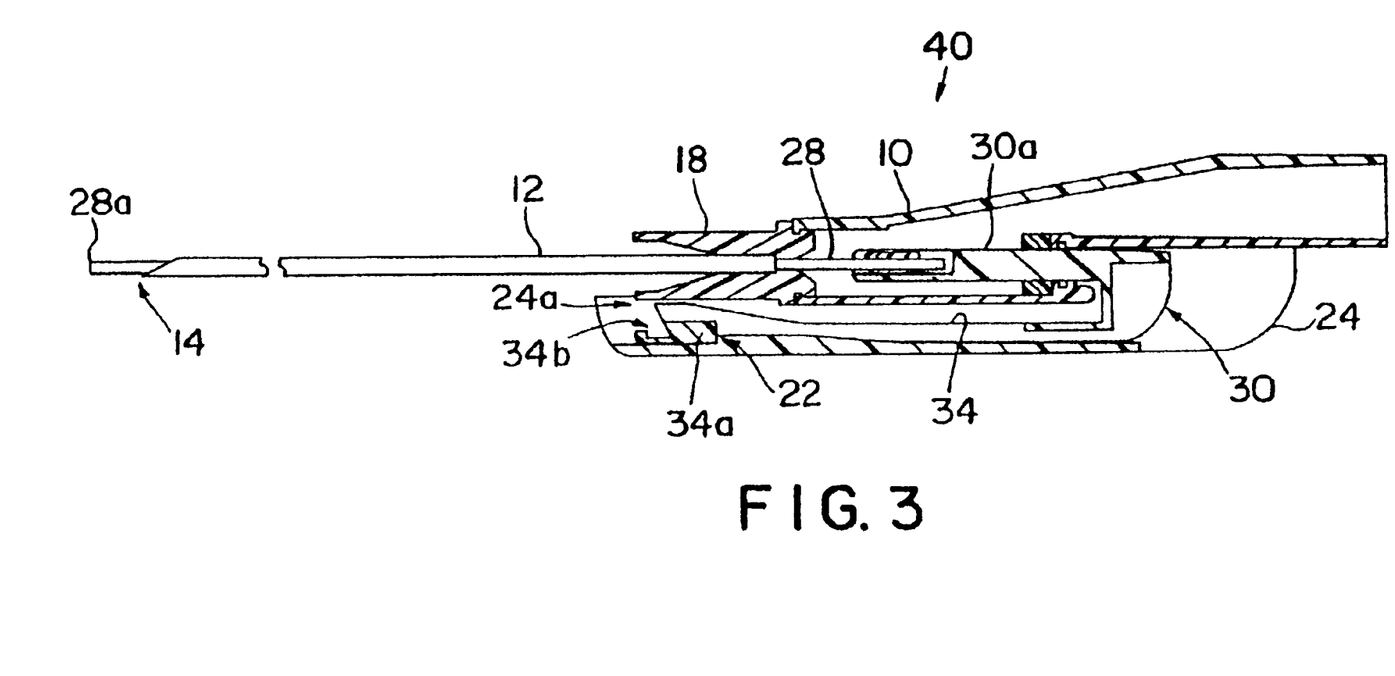
FIG. 3 is a schematic cross-sectional view of a needle assembly comprising the needle component of FIG. 1A and the blunting component of FIG. 2A.

Blunting probe 28 (FIG. 2A) is configured so that it can be inserted into probe port 18a (FIG. 1A) and thus be telescopically disposed within needle cannula 12. Piston portion 30a on shuttle 30 is configured to be movably received in port 18a (FIGS. 1A and 1B) and to form a seal with port 18a about bushing 54. The piston portion 30a thus extends into chamber 16a (FIG. 1A). Base portion 32 extends outside of chamber 16a where it carries detent 34 which comprises a lug 34a that is dimensioned and configured to engage stay 22 of needle component 10 (FIGS. 1A and 1B), as will be described below. Detent 34 also carries a coupling site 34b defined by an oblique flange 36 and a coupling shoulder 38. Shuttle 30 (FIG. 2A) is dimensioned and configured so that when blunting probe 28 is thus inserted into needle cannula 12 (FIG. 1A), detent 34 can be received within guide 24 and can move axially within channel 24a. The portions of shuttle 30 outside fluid chamber 20 are used to control the movement of the shuttle 30 and the blunting probe 28 thereon relative to the needle component 10. Shuttle 30 and guide 24 are dimensioned and configured so that detent 34 is biased to engage stay 22. Detent 34 is movable between a locking position in which it inhibits movement of the blunting component to an unlocked position in which it permits movement of the blunting component, as described further herein. Thus, needle component 10 and blunting component 30 can be assembled to produce a self-blunting needle assembly 40 shown in FIG. 3. FIG. 3 shows needle assembly 40 in the blunted configuration, i.e., with blunting probe 28 disposed telescopically within needle 12 and positioned therein so that blunt tip 28a protrudes beyond puncture tip 14 and thus blunts needle assembly 40. As illustrated in FIG. 3, lug 34a on blunting component 26 (FIGS. 2A and 213) outside of chamber 16a (FIG. 1A) engages stay 22 on needle component 10. Accordingly, even if axial pressure is applied on blunt tip 28a, movement of blunt tip 28a into needle cannula 12 (exposing puncture tip 14) is prevented because lug 34a of detent 34 bears against stay 22, thus preventing rearward axial movement (as sensed relative to needle cannula 12) of blunting probe 28. Thus, needle assembly 40 is locked in the blunted configuration in which it will protect users against accidental needle sticks. However, needle assembly 40 is releasably locked in the blunted configuration. To release the blunting component in needle assembly 40 as shown in FIG. 3, it is necessary to disengage lug 34a from stay 22. In the particular illustrated embodiment, guide 24 is dimensioned and configured to permit the flexure of detent 34 to permit lug 34a to be moved upward (as sensed in FIG. 3) for a distance sufficient to disengage lug 34a from stay 22. Once detent 34 has been flexed in this manner, blunting component 26 is free to slide within guide 24 for a distance sufficient for blunt tip 28a to be withdrawn into needle cannula 12, thus exposing puncture tip 14.

Figure 4A:
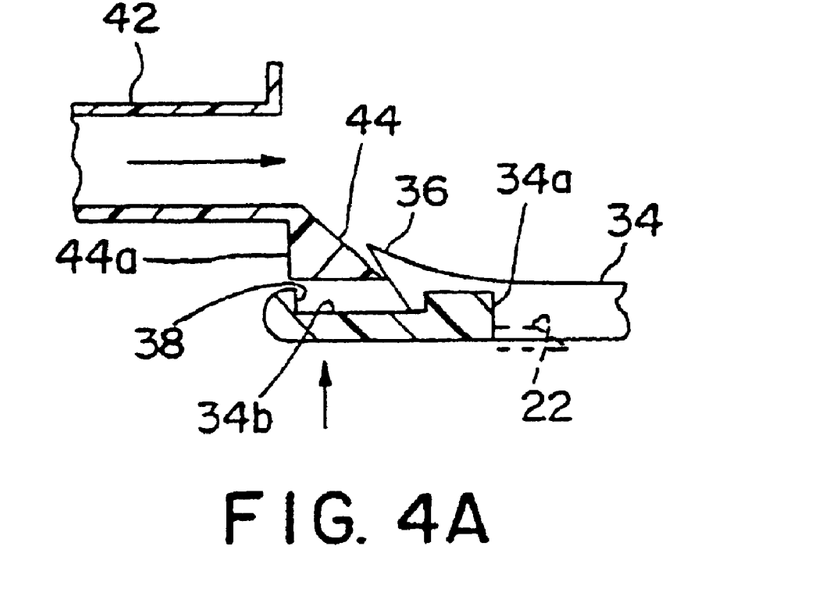
FIGS. 4A and 4B are schematic cross-sectional views illustrating the operation of a release accessory with the detent of the blunting component of FIG. 2A.
Figure 4B:
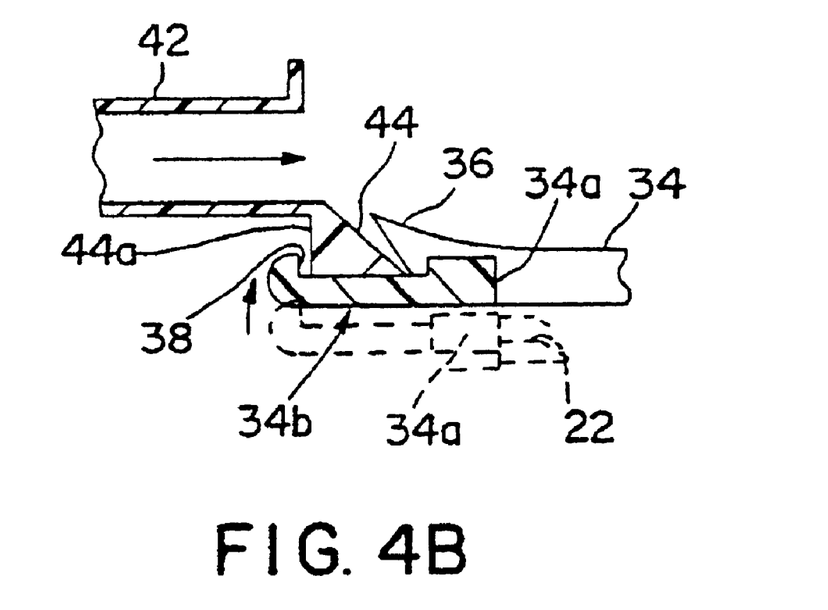

Guide 24 is open-ended so that detent 34 is accessible from outside guide 24. Coupling site 34b on detent 34 is especially accessible and is dimensioned and configured to engage an accessory device that is used to raise lug 34a away from stay 22. A suitable accessory is partially illustrated in FIGS. 4A and 4B. Accessory 42 carries a pawl 44 that is dimensioned and configured to enter channel 24a (FIG. 3) and to engage coupling site 34b. In particular, pawl 44 initially engages flange 36. Due to the slanted internal configuration of flange 36, movement of accessory 42 in a substantially rearward direction causes flange 36 to rise, as sensed in FIG. 4A, thus flexing detent 34 and lifting lug 34a, as indicated by the unnumbered arrows in FIG. 4A. Flange 36 and coupling site 34b are dimensioned and configured so that the rearward movement of accessory 42 flexes detent 34 to a degree sufficient to disengage lug 34a from stay 22 (shown in FIG. 3). When pawl 44 is fully received within flange 36, a coupling surface 44a on pawl 44 is disposed against coupling shoulder 38, as shown in FIG. 4B, which shows the elevated, disengaged (i.e., released) position of detent 34 and, in dotted outline, the locked position of detent 34. One advantage of the illustrated embodiment is that the releasable locking mechanism is enclosed within guide 24, thus reducing the likelihood of inadvertent release of blunting component 26, that could lead to, or allow, an accidental needle stick.

In some embodiments, such as a Y-line connector, an accessory has an injection port dimensioned and configured to receive the needle assembly and engage the coupling site. In other embodiments, such as a catheter, the catheter hub is dimensioned and configured to receive the needle assembly and engage the coupling site.

Figure 5A:
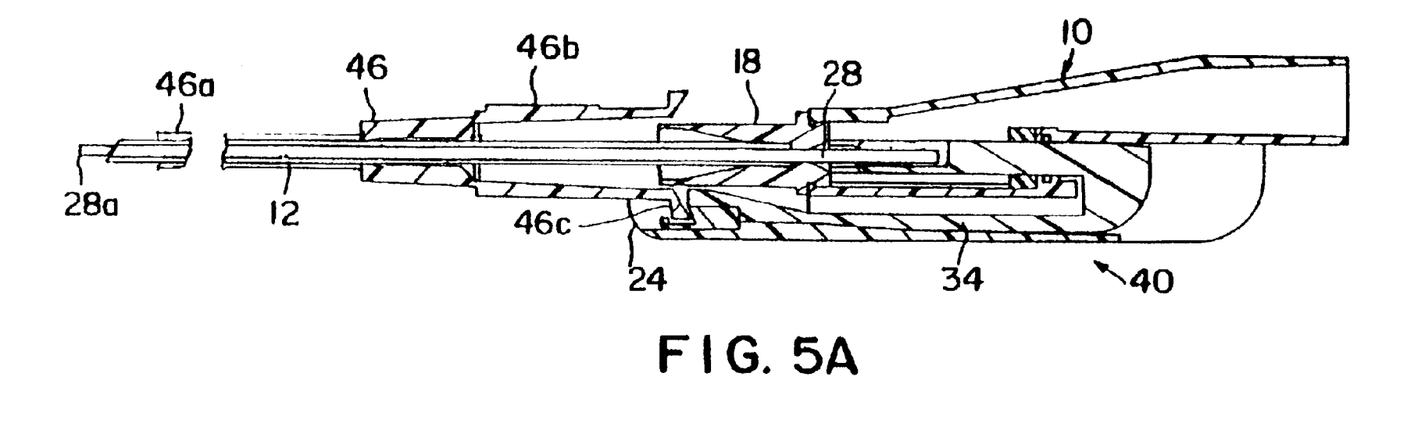
FIGS. 5A and 5B are schematic cross-sectional views of a self-blunting catheter assembly in accordance with one embodiment of the invention, comprising the needle assembly of FIG. 3 in the blunted and released configurations, respectively.

In a particular embodiment, an accessory may comprise part of a catheter assembly comprising a catheter hub on the end of a catheter tube. The catheter tube is sized to receive the needle cannula therein and the catheter hub is dimensioned and configured to engage the hub portion of the needle component. Thus, as shown in FIG. 5A, needle cannula 12, blunted by blunt tip 28a of blunting probe 28, is inserted into and through catheter 46. Catheter 46 comprises a catheter tube 46a and a catheter hub 46b which is dimensioned and configured to receive hub portion 18 of needle component 10. Hub 46b comprises an accessory flange 46c that is dimensioned and configured to enter U-shaped guide 24 and to engage the coupling site 34b on detent 34 as shown in FIGS. 4A and 4B.

The combination of catheter 46 and needle assembly 40 constitutes an accessory-needle apparatus in accordance with one embodiment of the present invention.

Figure 5B:
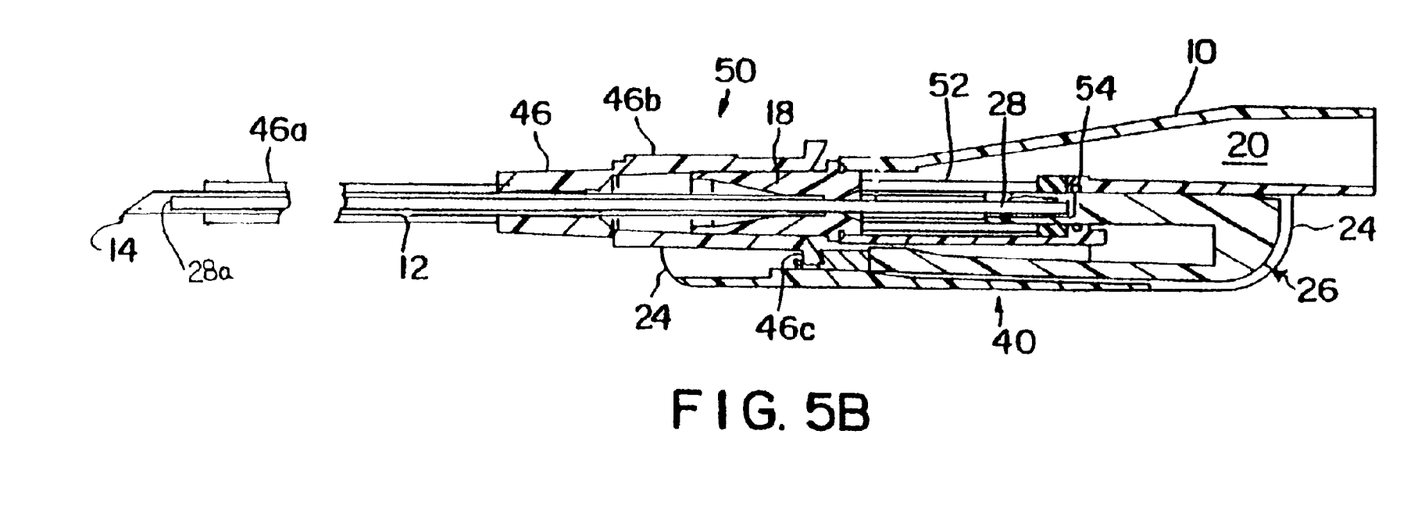

Catheter 46 and needle assembly 40 are dimensioned and configured so that, when catheter 46 is fully mounted on hub portion 18 of needle component 10, the end of catheter 46 is drawn past the puncture tip of needle cannula 12. To fully mount catheter 46 on needle assembly 40, catheter hub 46b is moved axially rearward along needle cannula 12. Such motion causes accessory flange 46c to engage coupling site 34b as shown in FIGS. 4A and 4B. Once accessory flange 46c engages coupling site 34b, a slight rearward motion of catheter hub 46b disengages lug 34a from stay 22. Further rearward motion of catheter tube 46 towards full engagement with needle component 10, as shown in FIG. 5B, moves blunting component 26 rearwardly (i.e., away from puncture tip 14 of needle cannula 12) and draws blunt tip 28a of blunting probe 28 into needle cannula 12, thus exposing puncture tip 14. As indicated above, blunting probe 28 is hollow and open only at the ends. Needle assembly 40 is configured, however, so that even when it is in the sharpened configuration shown in FIG. 5B, fluid can flow out of open end 28b, through slot 30b and into fluid chamber 20 of needle component 10.

In use, the fully assembled apparatus 50 in the sharpened configuration of FIG. 5B can be used to effect venipuncture with puncture tip 14 to introduce catheter tube 46 into the vein. Proper positioning of needle 12 into the vein is indicated by the flow of blood through needle cannula 12, into hollow blunting probe 28 and out the open end 28*b* (FIG. 2A) thereof, through slot 30*b* (FIG. 2A) and through access opening 52 (FIG. 5B) in needle component 10 to fluid chamber 20. As indicated above, needle component 10 comprises bushing 54 that is dimensioned and configured to engage shuttle 30 in a manner that permits movement of blunting component 26 between sharpened and blunted configurations while preventing fluid flow into U-shaped guide 24. This aspect of this invention thus pertains to an assembly in which the blunting component shuttle is disposed partially within a fluid chamber in the assembly, and is configured to extend from the interior of the fluid chamber to its exterior so that the blunting component can be manipulated by contact with a structure outside the chamber. In the embodiment illustrated, it is shuttle 30 which is dimensioned and configured for this purpose, but other embodiments will be obvious to those skilled in the art, after reading this disclosure.

After the catheter 46 is positioned as desired within the patient's vein, the needle assembly 40 is withdrawn from catheter 46. As needle component 10 is withdrawn from catheter hub 46*b*, accessory flange 46*c* pulls blunting component 26 forward in needle component 10 (i.e., towards puncture tip 14) by engaging coupling shoulder 38 (FIG. 4B). As lug 34*a* slides past stay 22 and needle assembly 40 is further withdrawn from catheter 46, lug 34*a* is moved into position to engage stay 22 and accessory flange 46*c* is disengaged from coupling site 34*b*. Accordingly, spring-like detent 34 moves downward, causing lug 34*a* to engage stay 22. This locks blunting component 26 in needle component 10 in the blunted configuration, i.e., with blunt tip 28*a* of blunting probe 28 extending beyond puncture tip 14. Due to the length of needle cannula 12 and blunting probe 28, needle assembly 40 becomes locked in the blunted configuration even before needle cannula 12 is fully withdrawn from catheter 46.

The location of stay 22 (FIG. 1A) and corresponding lug 34*a* (FIG. 2A) can be varied as matters of mere design choice. In addition, a variety of locking mechanisms that are releasable by the use of an accessory into which the needle is inserted can be employed.

Figure 6:
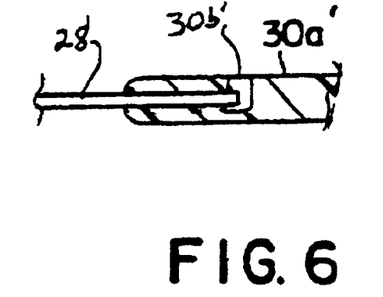
FIG. 6 is a partial cross-sectional view of a blunting probe and the piston portion of a shuttle member in accordance with another embodiment of the invention.
Figure 7:
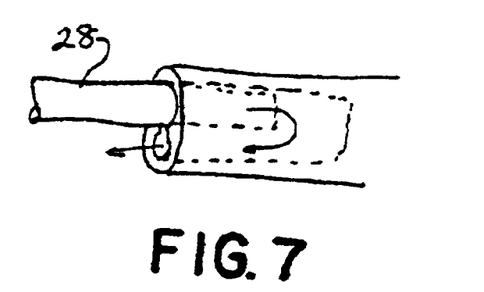
FIGS. 7 and 8 are partial perspective views of blunting probes and piston portions of shuttle members in accordance with two further embodiments of the invention.

The present invention can be practiced in various alternative embodiments, all of which permit fluid to flow from the open end of the blunting probe into the needle member chamber. For example, the piston portion of the blunting member shuttle, instead of being slotted, may be perforated by a two-ended bore as suggested in FIG. 6. In such an embodiment, the open end of blunting probe 28 is inserted into the opening of bore 30*b'* at the forward end of piston portion 30*a'*. Bore 30*b'* permits fluid to flow therethrough from the open end of blunting probe 28 to the needle component chamber. Optionally, the blunting probe may extend through the perforation in the piston portion so that fluid appears to flow directly from the open end of the blunting probe into the needle chamber. In an alternative embodiment, the cavity into which blunting probe 28 is inserted may be a non-perforating well configured to permit fluid to flow out the open end of blunting probe 28 and then forward along the blunting probe 28 and out the end of the piston portion, as suggested in FIG. 7.

Figure 8:
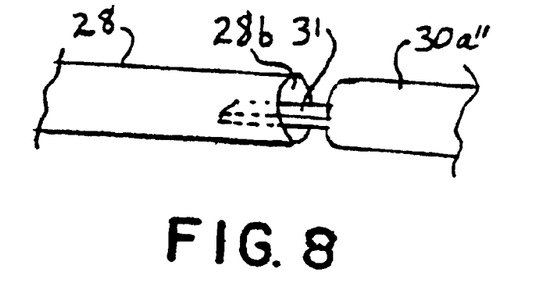

FIG. 8 shows an alternative configuration in which the piston portion 30*a"* carries a mounting extension 31*a* shaped like a chisel blade which is configured to be inserted and secured within the open end 28*b* of blunting probe 28 without blocking fluid flow therethrough. Various other mounting extensions can be used to permit the blunting member to be advanced and retracted by movement of the shuttle without obstructing fluid flow from the open end thereof into the fluid chamber of the needle member. For example, the mounting extension may be in the form of a helical spring, a substantially straight wire or rod, etc., joining the piston portion to the blunting probe without obstructing fluid flow from the end of the blunting probe.

Figure 9:
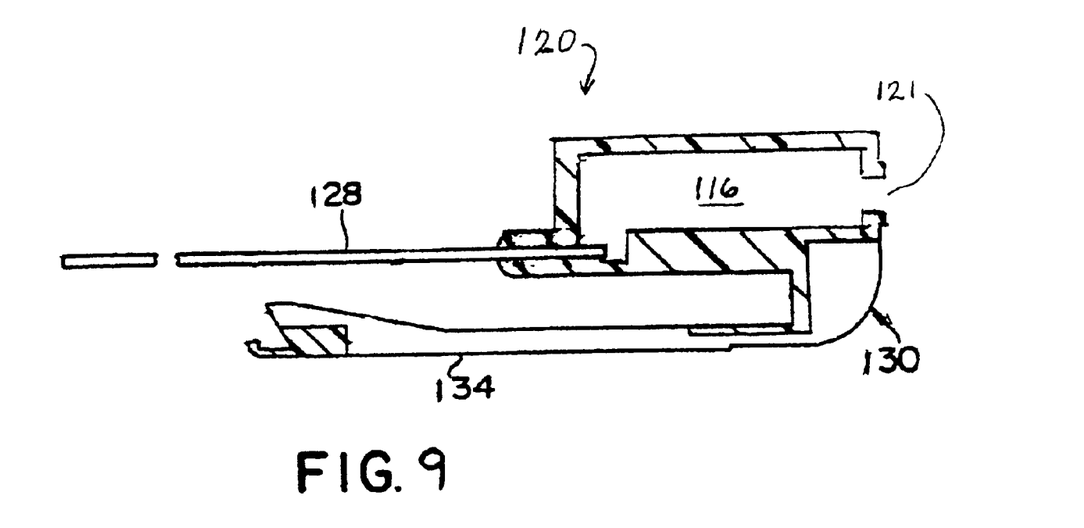
FIG. 9 is a schematic cross-sectional view of a blunting component for a needle assembly according to still another embodiment of this invention.

A blunting component for a needle assembly in accordance with yet another embodiment of the present invention is shown in FIG. 9. Blunting component 126 comprises a shuttle 130 on which is carried a blunting probe 128. Blunting probe 128 is hollow and open at both ends but is otherwise unperforated. Blunting probe 128 is mounted on shuttle 130 with an open end open for fluid flow to fluid chamber 116. Chamber 116 may define an opening 121 having a standard configuration for connection to other devices, e.g., a luer access. Optionally, part of the structure defining chamber 116 may be transparent or translucent, thus allowing chamber 116 to serve as a flash chamber. Shuttle 130 comprises a detent 134 which is configured for a releasable locking engagement with a needle component and, optionally, for engagement with an accessory device such as a catheter, in substantially the same manner as detent 34 (FIG. 2A) of shuttle 30. Thus, blunting component 126 and a complementary needle component can be configured so that blunting probe 128 is inserted into a needle cannula and is movable between a blunted configuration and a sharpened configuration, in substantially the same manner as apparatus 50, FIGS. 5A and 5B.

As is evident from FIG. 9, blunting probe 128 is mounted in a bore which perforates shuttle 130.

While the invention has been described in detail with reference to particular embodiments thereof, it will be apparent upon a reading and understanding of the foregoing, that numerous alterations and variations to the described embodiments may occur to those skilled in the art, and that such alterations and variations will lie within the scope of the appended claims.

What is claimed is:

1. A bluntable needle assembly comprising:

a needle component comprising a housing and a needle cannula mounted in the housing, the needle cannula having a sharp tip, wherein the housing defines a fluid chamber and an access port for fluid flow therethrough; and a blunting component comprising a shuttle member and a blunting probe received in a slot on the shuttle member, wherein the blunting probe comprises a hollow tube open only at the ends and a blunt tip, and wherein the slot is capable of fluid flow therethrough;

wherein the blunting probe is disposed within the needle cannula and wherein the needle component and the blunting component are configured for movement from a sharpened configuration to locking engagement in a blunted configuration; and wherein the shuttle member is configured to extend outside the fluid chamber and to permit fluid flow from the open end of the blunting probe into the fluid chamber.

2. The needle assembly of claim 1 comprising a detent and a stay engagement between the needle component and the blunting component, the detent being movable between (i) a locking position in which it may bear against the stay and prevent the needle assembly from moving to the sharpened configuration and (ii) an unlocked position which permits the needle assembly to move to the sharpened configuration.

3. The needle assembly of any one of claims 1 or 2 wherein the shuttle member defines a non-perforating cavity within which the blunting probe is mounted.

4. The needle assembly of claim 2 wherein the shuttle member comprises the movable detent.

5. The needle assembly of claim 2 wherein the detent further comprises a coupling site for engagement by an accessory device.

6. The needle assembly of claim 1 comprising a flash chamber.

7. A bluntable needle assembly comprising:

a needle component comprising a housing and a needle cannula mounted in the housing, the needle cannula having a sharp tip;

and a blunting component comprising a shuttle member and a blunting probe received in a slot on the shuttle member, the shuttle member defining a fluid chamber and an access port for fluid flow, and wherein the blunting probe comprises a hollow tube open only at the ends and a blunt tip, and wherein the slot is capable of fluid flow therethrough;

wherein the blunting probe is disposed within the needle cannula and the needle component and the blunting component are configured for movement from a sharpened configuration to locking engagement in a blunted configuration with a detent and stay engagement between them, the detent being movable between (i) a locking position in which it may bear against the stay and prevent the needle assembly from moving to the sharpened configuration and (ii) an unlocked position which permits the needle assembly to move to the sharpened configuration.

8. The needle assembly of claim 7 wherein the shuttle member comprises the movable detent.

9. The needle assembly of claim 7 wherein the detent further comprises a coupling site for engagement by an accessory.

10. The needle assembly of claim 7 comprising a flash chamber.

* * * * *